(12) United States Patent
Fischer

(10) Patent No.: US 10,352,911 B2
(45) Date of Patent: Jul. 16, 2019

(54) AIRBORNE ULTRASOUND TESTING SYSTEM FOR A TEST OBJECT

(71) Applicant: Balthasar Fischer, Vienna (AT)

(72) Inventor: Balthasar Fischer, Vienna (AT)

( * ) Notice: Subject to any disclaimer, the term of this patent is extended or adjusted under 35 U.S.C. 154(b) by 69 days.

(21) Appl. No.: 15/360,364

(22) Filed: Nov. 23, 2016

(65) Prior Publication Data

US 2017/0108472 A1    Apr. 20, 2017

Related U.S. Application Data

(63) Continuation-in-part of application No. 14/830,779, filed on Aug. 20, 2015, now Pat. No. 9,641,941.
(Continued)

(30) Foreign Application Priority Data

Sep. 12, 2008   (EP) ..................................... 08105330
Nov. 25, 2015   (EP) ..................................... 15196393

(51) Int. Cl.
   *G01N 29/22*   (2006.01)
   *G01N 29/24*   (2006.01)
   (Continued)

(52) U.S. Cl.
   CPC ....... *G01N 29/2431* (2013.01); *G01N 29/221* (2013.01); *G01N 29/2418* (2013.01);
   (Continued)

(58) Field of Classification Search
   CPC ............. G01N 29/221; G01N 29/2418; G01N 29/2431; G01N 29/28; G01N 29/32;
   (Continued)

(56) References Cited

U.S. PATENT DOCUMENTS 8,301,029 B2 * 10/2012 Fischer ................ H04R 23/008
                                                               398/133
9,417,147 B2 *  8/2016 Fischer ................... G01D 5/266
(Continued)

FOREIGN PATENT DOCUMENTS

DE           102004030154 A1 *  2/2006  ............. G01N 29/07

OTHER PUBLICATIONS

Daschewski, M. et al. "Physics of thermo-acoustic sound generation". Journal of Applied Physics, 114, 114903, Sep. 18, 2013, pp. 114903-1-114903-12. (Year: 2013).*

(Continued)

*Primary Examiner* — Michael A Lyons
(74) *Attorney, Agent, or Firm* — Nadya Reingand

(57) ABSTRACT

The Invention refers to an airborne ultrasound testing system for a test object (3) containing an ultrasound generator (1; 9) and an ultrasound receiver (2) and a control to control both and a computer assisted test result interface to display an image of the tested test object (3). The ultrasound generator (1) is a resonance-free thermo-acoustic ultrasound generator which does not rely on mechanically deformable or oscillating parts and the ultrasound receiver (2) is a membrane-free and resonance-free optical microphone in an air or gas coupled pulse echo arrangement or in an air or gas coupled transmission mode arrangement. With this testing system, it is possible to test objects with high precision and without liquids and disturbing ringing effects.

21 Claims, 7 Drawing Sheets

Related U.S. Application Data which is a continuation of application No. 14/176,088, filed on Feb. 8, 2014, now abandoned, which is a continuation of application No. 13/063,846, filed as application No. PCT/IB2009/053962 on Sep. 10, 2009, now abandoned.

(51) Int. Cl.
*G01N 29/28* (2006.01)
*G01N 29/32* (2006.01)
*G01N 29/34* (2006.01)
*G01N 29/46* (2006.01)

(52) U.S. Cl.
CPC .............. *G01N 29/28* (2013.01); *G01N 29/32* (2013.01); *G01N 29/343* (2013.01); *G01N 29/46* (2013.01); *G01N 2291/0258* (2013.01); *G01N 2291/056* (2013.01); *G01N 2291/102* (2013.01); *G01N 2291/106* (2013.01)

(58) Field of Classification Search
CPC ................ G01N 29/343; G01N 29/46; G01N 2291/056; G01N 2291/102; G01N 2291/106; G01N 2291/0258
See application file for complete search history.

(56) References Cited

U.S. PATENT DOCUMENTS

| | | | |
|---|---|---|---|
| 9,641,941 B2* | 5/2017 | Fischer | ............... H04R 23/008 |
| 2011/0048135 A1 | 3/2011 | Caron | |
| 2015/0233870 A1 | 8/2015 | Prinzhorn et al. | |

OTHER PUBLICATIONS

Pua, Chang Hong et al. "Non-membrane optical microphone based on longitudinal modes competition". Sensors and Actuators A, 168, Apr. 22, 2011, pp. 281-285. (Year: 2011).*

Daschewski, M. et al. "Influence of thermodynamic properties of a thermo-acoustic emitter on the efficiency of thermal airborne ultrasound generation". Ultrasonics, 63, Jun. 14, 2015, pp. 16-22. (Year: 2015).*

* cited by examiner

*Fig 2a:*  --Prior Art--
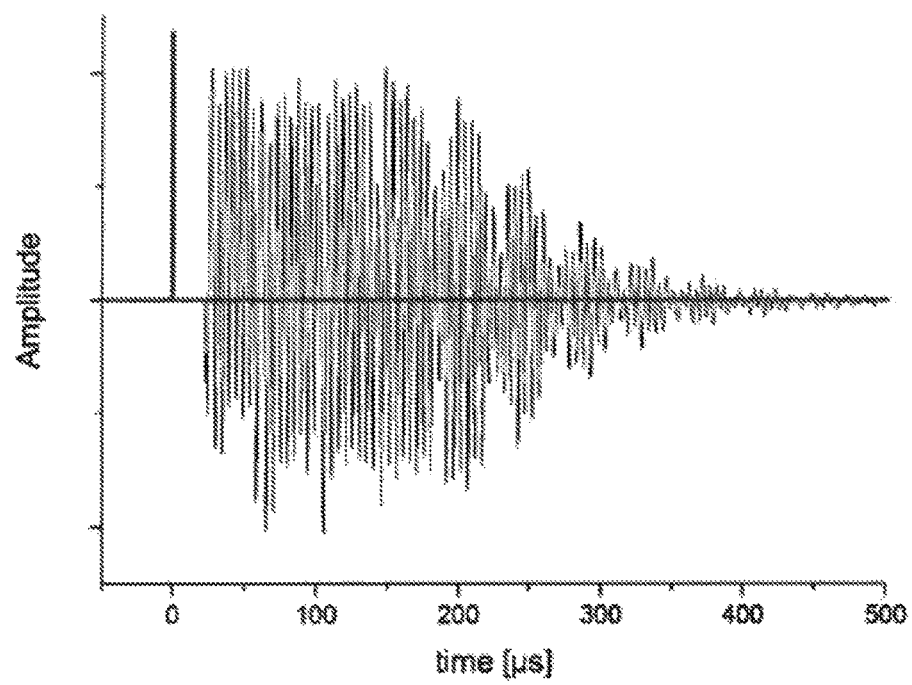
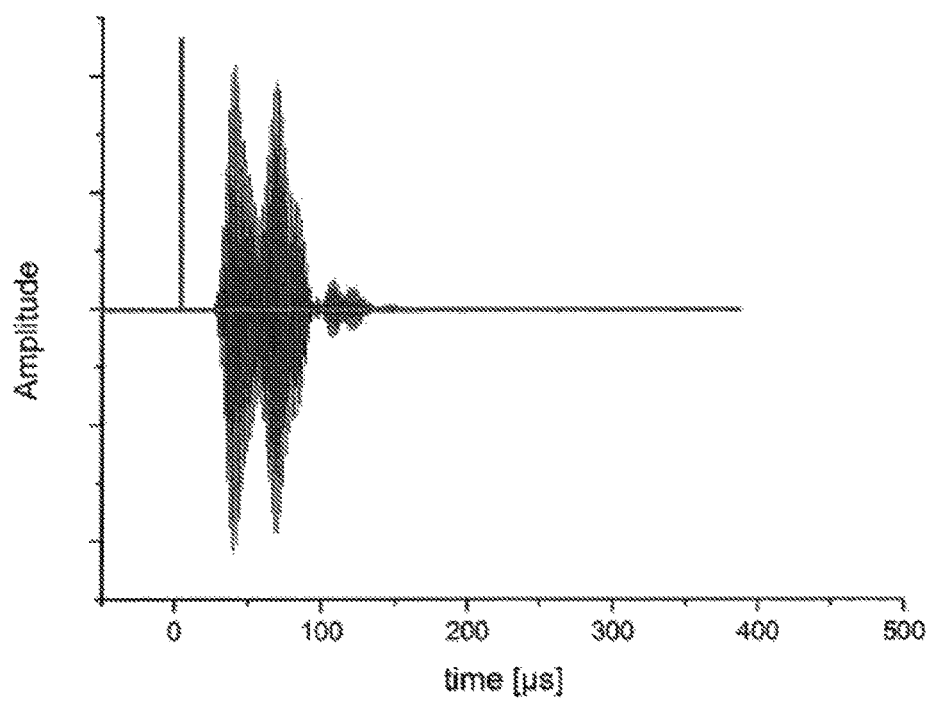

AIRBORNE ULTRASOUND TESTING SYSTEM FOR A TEST OBJECT

CROSS-REFERENCE TO RELATED APPLICATIONS

The present patent application claims priority to European patent application No. EP 15196393 filed on Nov. 26, 2015.

FIELD OF THE INVENTION

The present application is related to non-destructive systems and methods.

Non-destructive testing (NDT) methods to ascertain the mechanical integrity of components without inducing damage are crucial in various branches of industry for many years. For a variety of purposes, such as comprehensive quality control during manufacture, in-service inspection or in-service defect assessment and monitoring, it is not expedient to sacrifice test objects in the testing process. Such inspections are particularly critical for naval, aerospace, automotive industry or construction, where material failures can compromise human safety.

BACKGROUND

In these industry branches, the need for robust, durable lightweight construction has increasingly promoted the use of fiber-reinforced composite (FRC) materials, especially carbon fiber composites (CFC), during recent years. Compared to metals, they usually feature a complex, layered structure and therefore anisotropic material properties leading to a variety of different possible defect types that need to be reliably identified. Consequently, the development of NDT techniques suitable for these materials, preferably allowing a high degree of automation to save costs and increase reliability as well as testing speed, is of great importance.

A number of NDT methods have been developed so far. Based on the underlying physical detection mechanism, they mostly fall into a few broad categories: Magnetic Particle Inspection, Inductive or Eddy Current Inspection, Visual and Optical Inspection, Radiography and Thermography, Ultrasonic, as well as Sonic Inspection and Shearography. The first category is limited to ferromagnetic materials and therefore unsuitable for the inspection of FRC, while Eddy Current Inspection is applicable specifically to CFC since carbon fibers are conductive even though the surrounding matrix is usually not. Testing procedures belonging to all other categories have been assessed and implemented for FRC. Comparative reviews of NDT techniques for composite materials show that none of these technologies are equally applicable to the detection of each of the different defect types common in FRC at this point. While all methods have their advantages and drawbacks, some methods are inherently limited to certain test object geometries. Visual and Optical Inspection methods, for instance (with or without colored or fluorescent liquid penetrant) are limited to the detection of surface defects, with the exception of visible defects in transparent materials. Sonic Inspection methods typically suffer from comparably low sensitivity and spatial resolution. Shearography and Thermography are limited to the detection of near-surface defects.

Ultrasound methods (ultrasonic methods) and Radiography, on the other hand, are in principle capable of detecting and localizing both surface and bulk defects with high spatial resolution and sensitivity. However, for FRC, Radiography based methods, including high-resolution CT imaging, are not well suited to the detection of delamination defects, which constitute one of the most common defect classes in FRC, without use of an X-Beam (or Gamma) absorbing liquid penetrant. This, however, leads to significant complication of the procedures and limits the method to the inspection of surfaces or surface-near layers penetrable for the contrast liquid. Further in many test environments liquids are not wanted or not accepted.

Due to their versatility and good sensitivity, various ultrasound techniques are routinely applied for the inspection of FRC. Most of them employ piezoelectric transducers for generation of ultrasound pulses, their detection or both. While many specific methods to provide detection, imaging or volumetric localization of defects have been developed, distinguished by the exact configuration and number of transducers, they usually fall into two different operation modes. One approach is through-transmission mode, where the test specimen is placed between two piezoelectric transducers, acting as transmitter and receiver respectively. In this configuration, the receiver detects the attenuation of the primary ultrasound pulse due to defects. This configuration poses constraints on the specimen shape and also thickness due to the pronounced attenuation of ultrasound in FRC compared to metals. Alternatively, the pulse-echo method can be employed, where reflection or backscattering of the primary pulse due to defects is detected from one side of the sample. This method significantly facilitates applicability to complex-shaped test objects of varying thickness—as access to the test object is sufficient from one side only.

Conventional ultrasound testing systems employ a medium such as water or an emulsion or gel respectively to guarantee good coupling of ultrasound pulses to the test object. Allowing the use of ultrasound frequencies up to ~20 MHz, however, requiring immersion into a water basin or water jets between transducers and the specimen. Coupling fluids cannot be used for certain FRC structures or certain test environments, which creates need for non-contact test methods.

One actively developed option for contactless testing is the all-optical laser ultrasound method where an ultrasound pulse is created by absorption of a sufficiently strong laser pulse within the test specimen, and detection is performed interferometrically. A different approach is air-coupled ultrasound, similar to the conventional transducer-based method, but foregoing the coupling medium. This approach is enabled by increasingly sensitive highly resonant focused ultrasound transducers, allowing defect detection in spite of the decreased coupling caused by an air gap. While air-coupled systems using through-transmission mode are currently available, the implementation of an air-coupled pulse-echo configuration allowing one-sided tests of specimens poses significant problems. Highly resonant transducers oscillate for many periods both during pulse generation and detection, leading to a significantly increased "dead zone". This term denotes the surface-near region of the test object where defect detection is rendered impossible due to overlap between primary pulse, reflections from the sample surface and the actual signal contributed by backscattering from defects. For that reason, the skilled persons refrain from using this test method for precise material testing.

A contactless weld mechanical joint sample quality test procedure uses a square wave modulated laser beam to excite an ultrasonic impulse wave in the sample and measures its pulse amplitude interferometrically after propagation through the joint. The laser is moved towards and away from the test object. For the detection interferometrical methods which are known per se are used. The mechanically moving surface of the test object is scanned optically or the detection is done by means of a prior art microphone, without the use of any thermo-acoustic effect.

A measuring device for non-mechanical-contact measurement of a layer is known in the art, the measuring device including a light source operative to generate a pulse adapted to interact with the layer so as to generate a thermal wave in a gas medium present adjacent the layer, what makes use of the photo-acoustic effect. The thermal wave causes an acoustic signal to be generated. The measuring device further includes a detector adapted to detect a first signal responsive to the acoustic signal, the detector not being in mechanical contact with the layer. The first signal is representative of the measured layer.

A further method and arrangement for non-destructive evaluation of materials allows for the inspection of products without damaging the material. A continuous wave high-power laser sweeps across the material, using thermo-elastic expansion to create an ultrasound wave front on the surface of and in the material. Detection of the ultrasound from the test piece can be achieved by different methods, providing area, line or point detection, respectively. Point detection, where a single data point is capture at a time, is the typical method used for laser ultrasonics. Contact transducers can be used, but generally an optical detection method is used. Different interferometers have been used, including heterodyne (two beam), confocal Fabry-Perot, and photo-refractive quantum wells. A probe laser beam is directed to the detection point on the sample. The reflected light is gathered in an interferometer and sensed by a photodetector. Surface displacement caused by the ultrasound changes the interference of the light, which creates the signal. The detection point can be on the same side as the generation laser (pulse-echo) or the opposite side (through transmission). All these methods rely on deformations or spatial movements of elements in the sound detectors or microphones. Even with the favored line detection, in particular by Gas-coupled Laser Acoustic Detection, the ultrasound is sensed by directing a laser beam through the acoustic disturbance.

The disturbance by physical displacement causes a change in the optical path of the beam that can be detected with a position-sensitive photodetector.

Problems to be Solved

To summarize the problems occurring in the prior Art the following statements can be made:

The NDT testing systems introduced above have the following limitations or disadvantages:

i. in a non-airborne system, a contact medium other than air is required in principle between the test object and the testing system. However, especially for large-sized test objects, the application of a contact medium onto the test object is time-consuming and the contact medium can contaminate the test object. If water is used e.g. as a contact medium, the test object might rust/oxidize, which is not desirable.

ii. A conventional airborne ultrasound testing system is typically used in transmission mode. This requires physical accessibility from both sides of the test object which cannot be guaranteed in all testing environments. Especially for large-sized test objects or test object's which are installed in narrow compartments or the like, accessibility from two sides can be very challenging or Impossible.

Iii. If a conventional system is used in reflection mode (pulse-echo method), the post-pulse oscillations (ringing; see also FIG. 2) of the piezo which are typically used as sender and receiver limit the temporal resolution of the system and hence the depth-resolution. For instance, for a thin test object, or a thick test object with a defect close to the surface, the temporal sequence of the corresponding reflection signals may superimpose and thereby prevent an unambiguous signal analysis, which would be required for a sharp image of the test object. One also speaks of the so-called 'dead time' resulting in a "dead zone".

iv. Most test objects are absorbing higher ultrasound frequencies more than lower frequencies. On the other hand, a better resolution would be obtained with a higher frequency, since the corresponding smaller wavelength resolves small-sized internal defects with more accuracy. For this reason, in conventional systems, several ultrasound detectors of different quality are needed and used. A low-frequency receiver to enable thick test objects and a high-frequency receiver to enable a sharp image with a high spatial resolution. Conventional airborne ultrasound detectors have a very limited frequency bandwidth due to the highly-resonant design (required due to the fact that the receiver's sensitivity would be too poor for a non-resonant design). However, the use of several receivers at the same time might lead to mutual interference and a complex mechanical setup, and the sequential use of different configuration may lead to an Increase of testing time, which for most cases is undesirable.

v. In a conventional airborne testing system, the sensitivity of the detector typically scales with its size. This is for example true for a piezo receiver. Therefore, one needs a large-sized receiver in order to detect the potentially weak signal as the emitted ultrasound can be attenuated by scattering and absorption of the test object. However, the resolution of the image obtained by the ultrasound testing system is not only a function of the acoustic frequency, it can also be severely limited by the size of the receiver.

It is therefore a task of this invention to find a way of avoiding the need of contact media like liquid couple fluids in ultrasonic test environments and avoiding at the same time the drawbacks of the known air coupled (special contact media free) ultrasound material testing systems; such that an Airborne ultrasound testing system for a test object is created which can be used in a wide variety of test objectives.

SUMMARY

The technology described in the claims and in the following text allows these problems to be circumvented, and therefore to efficiently implement a single-sided pulse-echo ultrasound NDT method for FRC and similar materials. Similar materials in the sense of the invention cover all materials which can be tested with ultrasound. That includes parts made from one or more of the following elements: Wood, plastic, rubber, glass, ceramics, and metal. To bring different examples tires with metal wires embedded, IC-Boards, air plane wings, door panels, coaxial cables etc.

The invention solves all problems discussed in part 3. The proposed ultrasound testing system contains a resonance-free thermo-acoustic ultrasound generator (emitter). Examples and explanations can be found at Daschewski, M. et al "Resonanzfreie Messung und Anregung von Ultraschall," In Technisches Messen, 82(3) (2015), which is incorporated in its entirety by reference herewith. It further contains a membrane-free and resonance-free optical microphone. Such microphones are free from mechanically deformable parts and detect the sound-pressure induced alteration of the refractive index of the medium, preferably a gaseous or fluid medium. Examples and explanations can be found in PCT Patent applications WO2008000007A1, WO2010029509A1, WO2012163681A1, all having the same inventor as the present application, all of which are incorporated by reference in their entirety herewith especially with regard to the drawings and description of the drawings in WO2008000007A1, WO2010029509A1, WO2012163681A1. Further example is represented by the product line Eta of the company XARION, Vienna, Austria. Such optical microphones work in a range from 10 HZ up to 1 MHz in air, and up to 25 MHz in liquids which make them very suitable for ultrasound detection. Generator and microphone are—according to the invention—in an air coupled pulse echo arrangement or in an air coupled transmission mode arrangement. A thermo-acoustic generator is an ultrasound generating device, which does not rely on mechanically deformable or physically oscillating parts but generates ultrasound by quickly sequentially heating and cooling its surface. Said generated ultrasound then emits onto or through the test object. A transducer involving oscillating mechanically deformable elements would be a transducer based on a piezo crystal or a loudspeaker membrane, for example. However, such transducers with mechanically deformable elements have the problems mentioned above and are not favorable for that reason.

Seen from a broader perspective of the invention, also the combination of a laser beam and a material sample, or the combination of a laser beam and the test object itself, can be regarded as a resonance-free thermo-acoustic ultrasound generator. Hereby, the laser beam of preferably high-intensity is operated in pulsed mode, so that the laser-radiation of the short pulse or the sequence of several short pulses are generating a thermo-acoustic shock-wave due to interaction with a target material. The target material sample can for instance be any plate, introduced between said surface of the test object and the laser pulse source, or it can be the surface of the sample itself. Furthermore, said target material can also be a material layer buried inside the test object, for instance a specific light-absorbing matter inside the test object.

A membrane-free and resonance-free optical microphone is an all-optical sound pressure detector. It does not rely on mechanically deformable parts (such as a plezo crystal or a microphone membrane) since it detects pressure variations by optical means based on an interferometric read-out of the optical wavelength alteration caused by the sound-pressure induced alteration of the refractive index of a gaseous or fluid medium. Said type of sound detector has the further advantage of being resonance-free, thereby significantly reducing or preferably totally omitting any "dead zone".

Due to the use of airborne ultrasound waves, for the proposed apparatus, a contact-free examination of the test object is possible. No contact medium such as water or gel is required. Furthermore, the proposed apparatus allows a one-sided testing of the test object. The accessibility from two sides is therefore not required but still possible. Also, the thermo-acoustic generator used in combination with the membrane free optical microphone in the proposed apparatus does not show ringing effects as the prior art testing equipment is typically exhibiting (also see FIG. 2), but is able to emit a very short Dirac-alike excitation signal on the order of a few us or even below 1 µs. By Dirac-alike excitation pulse, a signal similar to the mathematical Dirac function is meant, in other words, an infinitely thin excitation spike. This behavior also applies for the thermo-acoustic wave induced by laser excitation. The same holds true for the optical microphone used as signal detector: it does not show ringing effects either and therefore can detect very short Dirac-alike ultrasound signals without adding artificial temporal signal broadening. Due to this true temporal impulse response of the proposed testing apparatus, thin materials can be examined as well as defects of thick test object's even if they are located close to the surface. No dead time and no temporal signal-shading effects occur. According to the Fourier theorem, the short impulse emitted by the thermo-acoustic generator contains a large frequency bandwidth. On the other hand, the optical detection system (i.e. the optical microphone) is also characterized by its very large detection bandwidth of several MHz. Therefore, the device according to the invention is capable to process low and high frequencies at the same time. This enables the examination of thick-sized test objects while at the same time enabling high spatial resolution. Furthermore, the apparatus can be very small-sized (also see FIG. 3), therefore not disabling the very high spatial resolution of the image.

Optical microphones can be found in the PCT patent applications WO2008000007A1, WO2010029509A1, WO2012163681A1 which are incorporated herein by reference especially with regard to their drawings and specification explaining said drawings.

A practical example of such useful optical microphone has been developed at XARION Laser Acoustics GmbH from Vienna, Austria.

However, the invention is not restricted to any special type of optical microphone. Preferably, the fiber-coupled embodiment of the optical microphone, the Eta product series-type of Xarion Laser Acoustics GmbH, is used best for the objective aim.

BRIEF DESCRIPTION OF THE DRAWINGS

The drawings are described in an overlapping method. Same reference numerals refer to same elements.

FIG. 2A shows the signals including ringing of known testing devices

DETAILED DESCRIPTION OF THE PREFERRED EMBODIMENT

Figure 1:
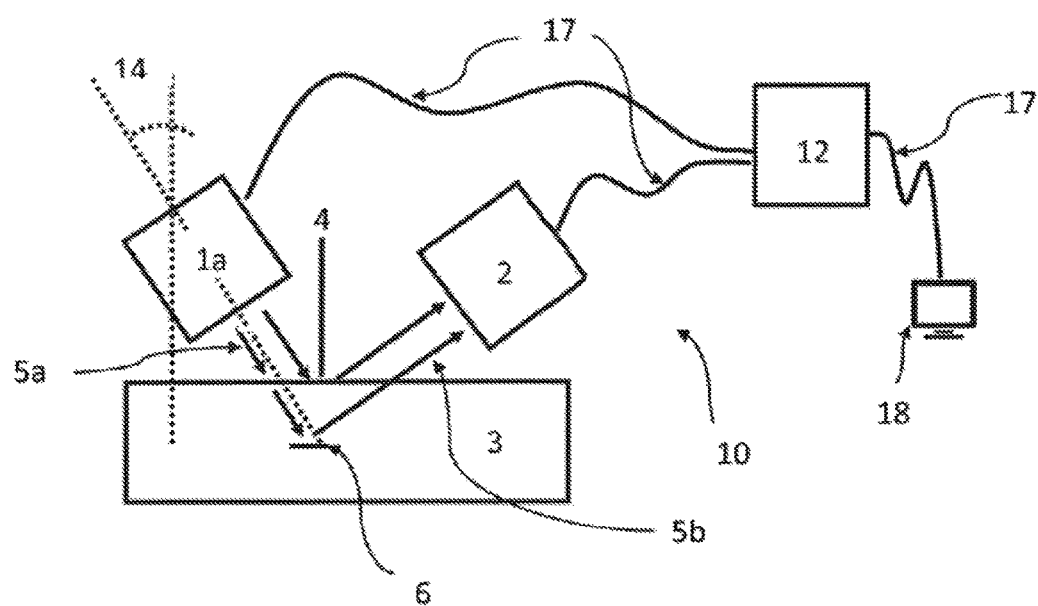
FIG. 1 shows a typical inventive apparatus.

A typical inventive apparatus is shown in FIG. 1. Airborne ultrasound waves 5a are emitted from a thermo-acoustic generator 1a into air or into another sound-propagating medium such as a specific gas 10 which might be in the test environment. Such specific gas may, for example, include nitrogen or carbon dioxide or a gas mixture e.g. Thorlabs Gas (inert dusting gas) available from Thorlabs Inc., which may be favorable due to the fact that the test object 3 will not be exposed to oxygen; it can also be favorable since it augments the sensitivity of the membrane-free and resonance-free and resonance-free optical microphone due to the fact that the pressure-dependent change of refractive index is dependent on the medium. The sound-propagating medium may also be any liquid (such as oil, water or blood or other); however, the efficiency of the thermo-acoustic generator is favorable if used in gas. By consequence, the sound propagating medium will typically be regular, environmental air. The sound waves are incident on the test object 3. Due to reflection from the front or rear surface of the test object, or from internal defects 6 or from any particularly ultrasound reflecting parts, the sound waves are detected by the receiver 2. Such parts could be e.g. loose filaments of a fabric, cracks in a compound material as well as elements in an smd integrated circuit or discrete parts on a mother board of a computer or the like. Furthermore, delamination inside a layer-compound can be detected, even if, from the exterior, no damage is visible.

With the invention one could on the other hand also inspect e.g. cracks in carbon rods or uranium rods submersed in heavy water or the like. There the airborne device might be submerged into the reactor vessel. Hence the invention can be used in a wide variety of test objectives within gases or within liquids.

A shielding wall 4 can be positioned between the generator and the detector in a spatial relationship as to be used to isolate the unwanted direct sound, for instance the sound reflected from the surface of the test object or the sound from the sound source (generator/emitter). Typically, a control unit 12 consisting of hardware and software is used for the generation of the electric pulse signal, the analysis of the electric signal as obtained by the receiver 2 and for the generation of an image of the test object.

More specifically, the hardware consist of (i) an arbitrary signal generator which is able to generate the electric excitation pulses sent to the generator 1a and (ii) a signal-analysis hardware (typically an analog-to-digital converter and optionally a digital signal processing unit such as a DSP chip) receiving its input from the detector 2, and (iii) a mechanical scanner (refer to FIG. 7) to physically move the generator 1a and the detector 2 over the surface of the test object, and, furthermore, (iv) a software routine capable of controlling at the same time the signal generator, the signal analysis hardware, the scanner, while processing and combining the amplitude, temporal and spectral data stream. More specifically, it can analyze the spectral information of the received signal using a Fourier Transform. Due to the broad spectral bandwidth of both, the generator and the detector, many frequencies can be emitted and received at the same time. Hence, by using spectral analysis as part of the signal processing, many frequency bands can be investigated at the same time. Hereby, multiple, sequential scanning procedures (each using different distinct frequencies, as common in state-of-the-art devices) can be avoided. Such a control unit 12 can either be a commercially available device (such as a Dr. Hillger USPC 4000 AirTech (scanner), Hill-Scan 3010 (converter) and Hilgus (software) available at Ingenieurbuero Dr. Hillger, or it can be a specifically built system. The control unit 12 is connected with an electrical connection 17 to a computer system 18 for data logging/recording, signal analysis, further processing and display via monitor.

Further reference numerals used in FIG. 1:
1a: Thermo-acoustic ultrasound generator
2: Membrane-free and resonance-free and resonance-free optical microphone (ultrasound receiver)
3: Device under test, test object, material sample
4: Optional shielding wall
5: Ultrasound pressure wave 5a from generator 1a, 5b to receiver 2
6: Material defect
10: Medium in test environment: air or other gases or other fluids
12: Control unit
14: Angle, exemplary for different angles for the different elements of the ultrasound generator and receiver. E.g. receiver 2 is likewise in a particular angle directed to a vertical/normal on the surface of the test object 3. This angle is not shown in the drawing and may vary depending on the shown angle 14 of the ultra sound generator but also on other physical matters as e.g. the material sample. The user will in practice vary the angle 14 and the respective angle of the receiver 2 so that the received signal is a maximum or close to a maximum. Preferably, the generator 1 and/or the receiver 2 are—when in use—spatially positioned relative to a vertical plane on the surface of the test object 3 in an angle 14 to face a test object 3. According to an optional feature of the invention, said angle 14 can be varied with respect of the relative position of the generator 1 and/or the receiver 2 to said vertical plane on the test object 3.
17: electrical wire
18: computer system.

Possible variations of the device of FIG. 1:

The angles 14 between generator 1a and test object 3 (more precisely: the angle formed between the axis of the emitted ultrasound and the surface normal of the test object), or the receiver 2 and test object 3 may be varied in order to maximize a certain signal component. Note that the angle 14 as indicated in FIG. 1 does not only apply to the specific element where it has been indicated but to all angles relevant for the skilled person in the field of ultra sound measurement. That includes the angle between a straight line (direction of emission) from the generator to the surface of a test object and a straight line from the receiver (direction of reception) to the test object. Also, the angle of any other element used in the apparatus may be varied. The angles of each component may be identical or different from each other, according to desired effect in terms of performance. In order to vary said angle, the generator 1a is rotated with respect to test object 3 so that the sound waves are incident onto the test object under a different angle, with could be more any angle between 0° (180°) and 90°. The same applies for the angle between the receiver 2 and the test object.

The distance between generator 1a, receiver 2 and test object 3 may be varied in order to maximize a certain signal component. In order to vary said distance, the generator 1a and the receiver 2 are physically placed closer (e.g. a few mm) to each other, or, placed further away (e.g. several meters) from each other. The same applies for the distance between the generator and the test object, and/or the receiver and the test object, respectively.

Generator 1a and receiver 2 might be mounted on one carrier or on different carriers, and the generator 1a and the receiver 2 may even be placed on opposing sides of the test object 3, resulting in a transmission-setup measurement.

FIG. 2A (prior art) shows in the upper part signals emitted from a conventional 200 kHz piezo ultrasound generator and below a conventional 500 kHz generator (right). Electric stimulus (thick line) and corresponding emitted ultrasound signals as emitted from the piezo generators are shown. Even though the electric stimulus is very short (in this example it has a length of 2 µs), the resulting sound signal can have a length of several 100 µs, because a piezo crystal shows a serious ringing effect due to its self-resonance.

Figure 2B:
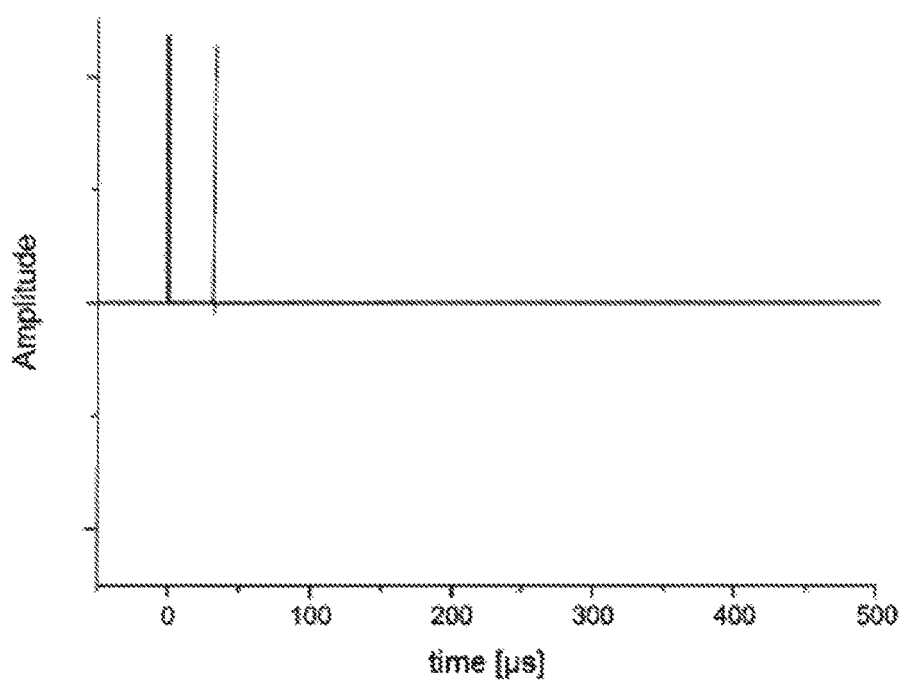
FIG. 2B: shows the ringing free signals from a thermo-acoustic transducer, employed by the invention in combination with a membrane-free and resonance-free laser optical microphone.

FIG. 2B illustrates the acoustic signal emitted from thermo-acoustic generator as measured by a membrane-free and resonance-free and resonance-free optical microphone. Electric stimulus (thick line) and corresponding acoustic signal are shown. Neither the thermo-acoustic generator nor the optical microphone show self-resonance behavior, since both transducers are not based on mechanically moving parts, detect the sound-pressure induced alteration of the refractive index of a gaseous or fluid medium. Therefore, the recorded signal is very short and corresponds to a high degree to the electric stimulus. A conventional state of the art piezo receiver could not be used for detection without adding undesired mechanical resonance effects. Furthermore, a conventional capacitive microphone would not have enough frequency bandwidth (typically limited to 140 kHz), to record this short pulse of a length of 2 µs which requires at least a bandwidth of ½µs=500 kHz.

Figure 3A:
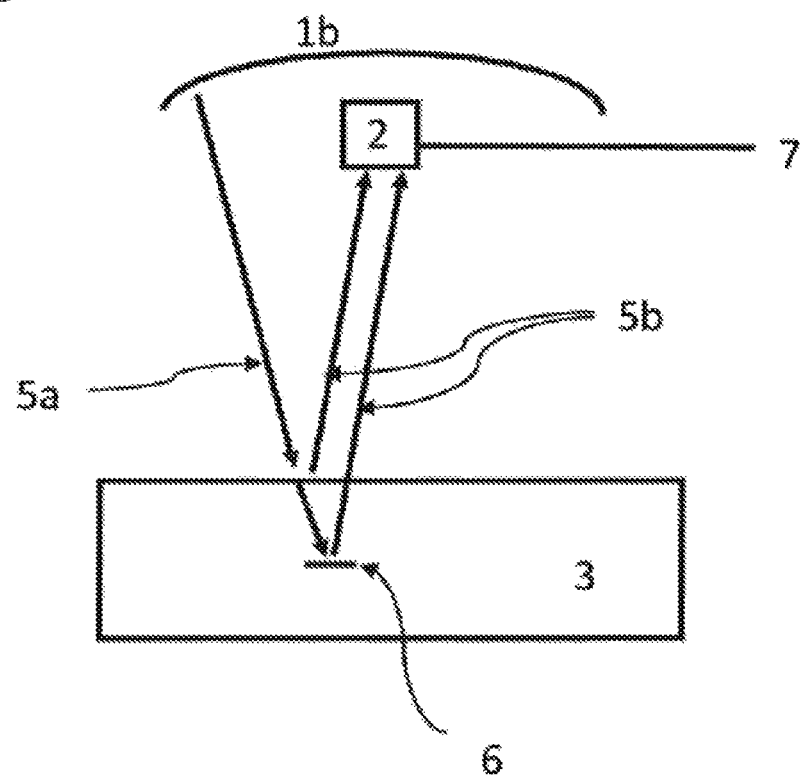
FIGS. 3A and 3B shows a focusing embodiment.
Figure 6:
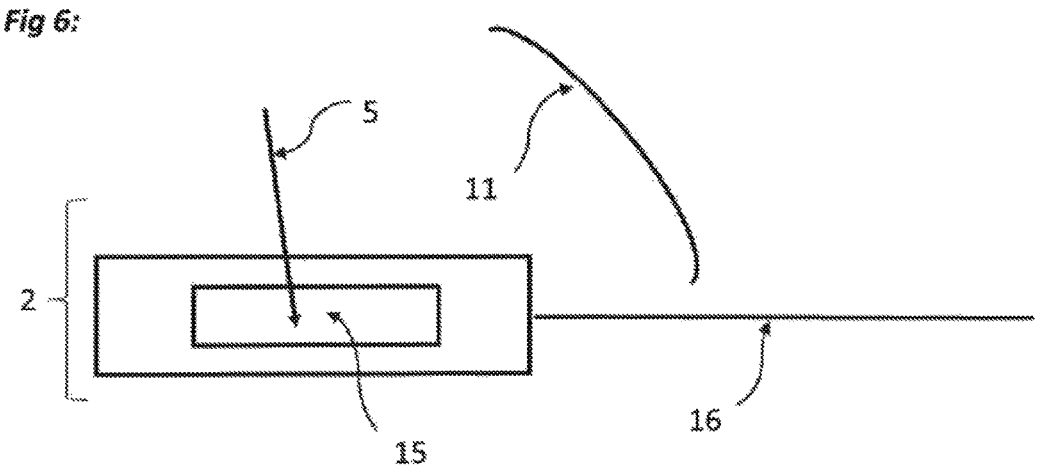
FIG. 6 shows the configuration of a membrane-free and resonance-free optical microphone.

FIG. 3A shows a focusing embodiment which might be employed in order to facilitate a well-directed excitation air pressure wave. Preferably, the generator $1b$ is built as a concave curved generator, wherein especially the generator $1b$ has a parabolic emitting element. Due to the fact that the thermo-acoustic generator $1b$ uses a very thin foil on the order of µm-thickness, it can be formed into the shape of a curved, especially parabolic emitter. The generator $1b$ could also be mounted in front on an especially concave emitter-mirror, which reflects the ultrasound waves onto the test object. Hereby, it is possible to focus the emitted ultrasound signal onto a small-sized spot on the test object 3. This allows a higher spatial resolution. The receiver 2 may be placed in front of the generator $1b$ via a thin mechanical mount 7, since the receiver is of small size and does not substantially shade the emitted signal from the generator. The receiver typically contains a hollow chamber or has at least one through-hole 15 (see FIG. 6) through which—in an improved variant—the emitted sound pressure wave 5a from the generator $1b$ may propagate towards the test object, and through which also the reflected sound pressure waves 5b may propagate. In FIG. 6, this through-hole 15 is shown in detail. Due to this setup, which gets the shape of a handy probe where generator and microphone are integrated, the apparatus may be of very small physical size. The generator $1b$ could, as an extreme, not be larger than the footprint of the detector 2. The acoustic waves 5 should be radiated through the detector 2 hereby forming an apparatus of minimal lateral dimensions.

Further reference numerals used in FIG. 3A:
$1b$: Thermo-acoustic ultrasound emitter/generator
2: Membrane-free and resonance-free optical microphone (ultrasound receiver)
3: Test object, material sample
5: Ultrasound pressure wave
6: Material defect
7: Mechanical mount.

Figure 3B:
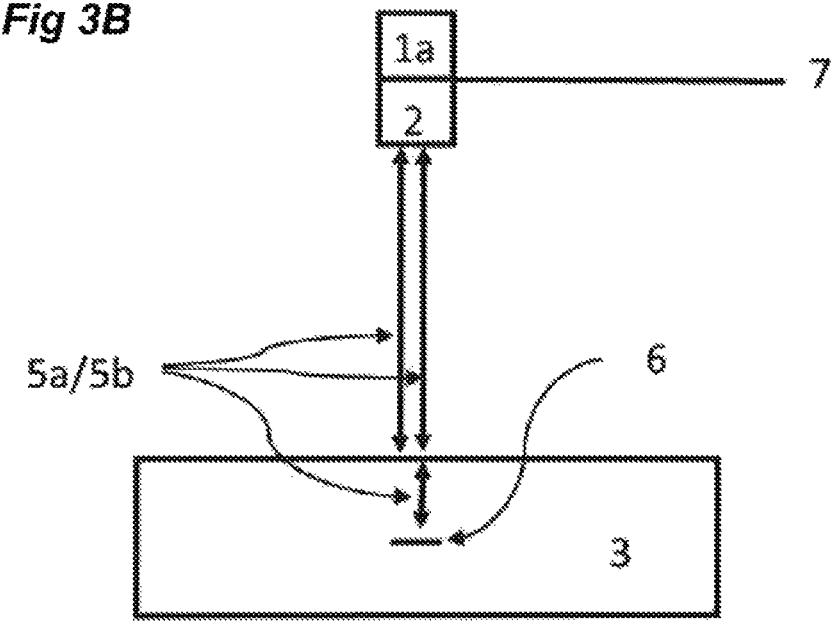

Possible variations of the device of FIG. 3B:
a. —the angles 14 (see FIG. 1) between generator $1a$ and test object 3, or receiver 2 and test object 3, or generator and receiver may be varied in order to maximize a certain signal component;
b. —the distance between generator $1a$, receiver 2 and test object 3 may be varied in order to maximize a certain signal component;
c. —the surface shape of the generator $1a$ may be varied. It may be smaller or larger, according to the required sound pressure level, or, it may take the shape of a sphere, of a plane, of a parabolic mirror or other useful shapes for the concentration of creating the ultra sound pressure wave;
d. —the surface shape of the receiver 2 may be varied as well. It may be smaller or larger, according to the required detector sensitivity, or, it may take the shape of a sphere, of a plane, of a parabolic mirror or other in order to guide or reflect the returning sound wave into the hollow chamber of the optical microphone;
e. —additional mirror elements may be placed in front of (or: behind of) the generator $1a$ or the detector 2; also, refer to FIG. 4 for a more thorough explanation of the mirror elements. These mirror elements can be planar or have a curved surface (for instance a parabolic shape); the mirrors may contain holes for sound excitation wave transmission, if required;
f. —the receiver 2 could be mounted in front of the generator $1a$ via a mechanical mount 7, so that emitting direction and receiving direction of the air pressure waves 5a/5b are at least substantially parallel.

Figure 4:
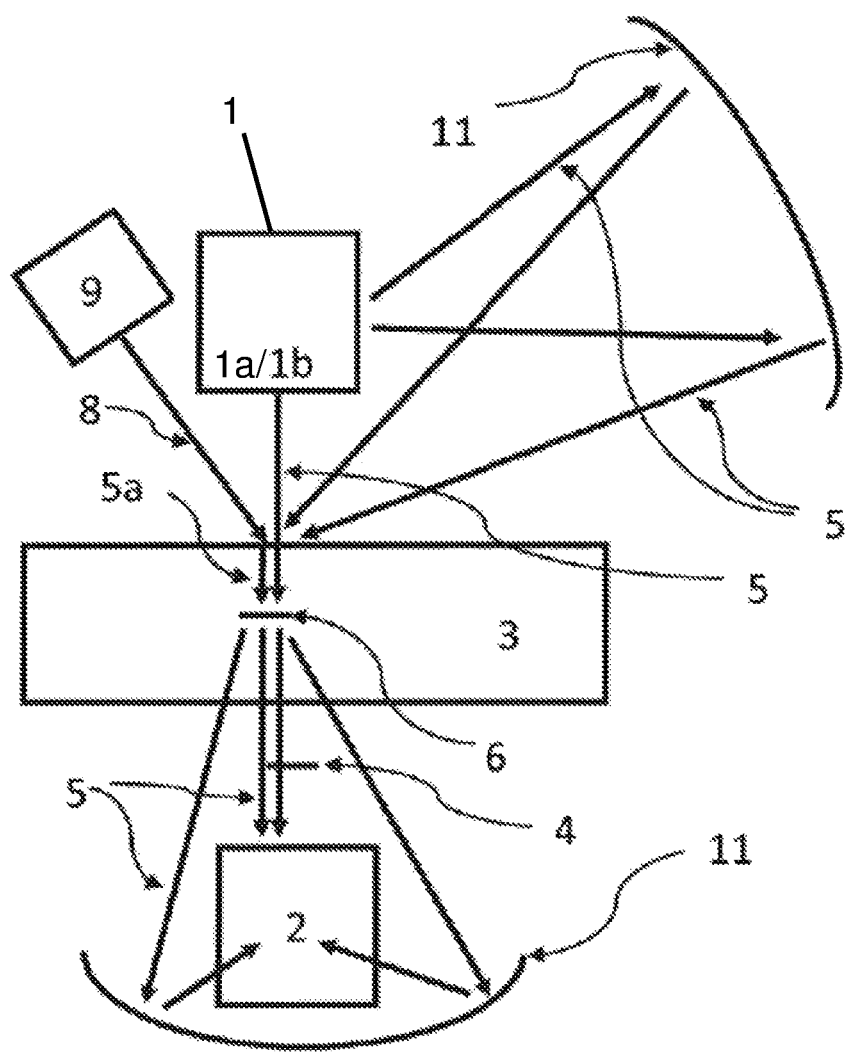
FIG. 4 shows a different apparatus.

FIG. 4 shows a different apparatus, where the generator $1a$ and the receiver 2 may be placed on opposing sides of the test object 3, resulting in a transmission-setup. Instead of the generator $1a$ also here, an alternative source of ultrasonic wave, a laser 9 can be used. Note that generator $1a$ and laser 9 are usually not being used at the same time, but they may replace each other, respectively. Also, note that the generator $1a$ can either take the shape of generator $1a$ or generator $1b$ (see FIG. 3A), and is hence simply called generator or emitter 1. Also, refer to FIG. 5 for a more detailed description using the laser beam 8 emitted by a laser 9 as an ultrasonic wave generation.

Reference numerals in FIG. 4:
1: Thermo-acoustic ultrasound generator
2: Membrane-free and resonance-free optical microphone (ultrasound receiver)
3: Test object, material sample
4: Optional shielding wall
5: Ultrasound pressure wave
6: Material defect
8: Laser beam, generating a thermo-acoustic shock 5 wave at the surface of the test object 3
9: Laser
11: Mirror element.

Possible variations of FIG. 4: the angles 14 (see FIG. 1) between generator $1a$ and test object 3, or receiver 2 and test object 3, or generator and receiver may be varied in order to maximize a certain signal component:
  the distance between laser 9, receiver 2 and test object 3 may be varied in order to maximize a certain signal component
  the laser 9 may be operated in different pulse-length modes (ps, ns, and other) and at different optical wavelengths (e.g. at 1064 nm, 532 nm, the far-infrared, and other).
  the surface shape of the receiver 2 may be varied. It may be smaller or larger, according to the required detector sensitivity, or, it may take the shape of a sphere, of a plane, of a parabolic mirror or other.
  additional mirror elements 11 may be placed in front of (or: behind of) the detector 2. These mirror elements can be planar or have a curved surface (for instance a parabolic shape). The mirrors may contain holes for sound transmission, if required. The mirror elements serve the following purpose: as for the generator 1, sound waves may be radiated in a non-directive manner. This is to say, the sound waves may be radiated not only towards the test object 3, but also in other spatial direction. The mirror collects these sound waves and focusses them onto the surface or inner areas of the test object. Hereby, the intensity of the soundwave incident onto the surface of the test object is maximized, which in many application is desirable. As for the detector 2, the purpose is similar: since the sound waves Irradiated from the test object 3 may be directed in several spatial directions and potentially get lost by not being incident onto the detector 2. The mirror element 11 is collecting these sound waves and redirecting them onto the aperture of the detector (hollow chamber 15). Due to the additional path length, the reflected wave needs to travel, the reflected signal can be temporally delayed compared to the direct sound which hits the detector 2 without the detour via mirror element 11. This may, due to the short temporal delay for instance, not be of importance; or, the subsequent signals can be isolated using temporal gating methods. Furthermore, the detector 2 can be shielded using am acoustic shield 4, so that no direct signal is incident onto it. Yet another possibility is that the detector is placed away from the location where noticeable direct sound is emitted onto the detector, and that the main portion of the ultrasonic wave can only reach the detector via the mirror element 11.

Figure 5:
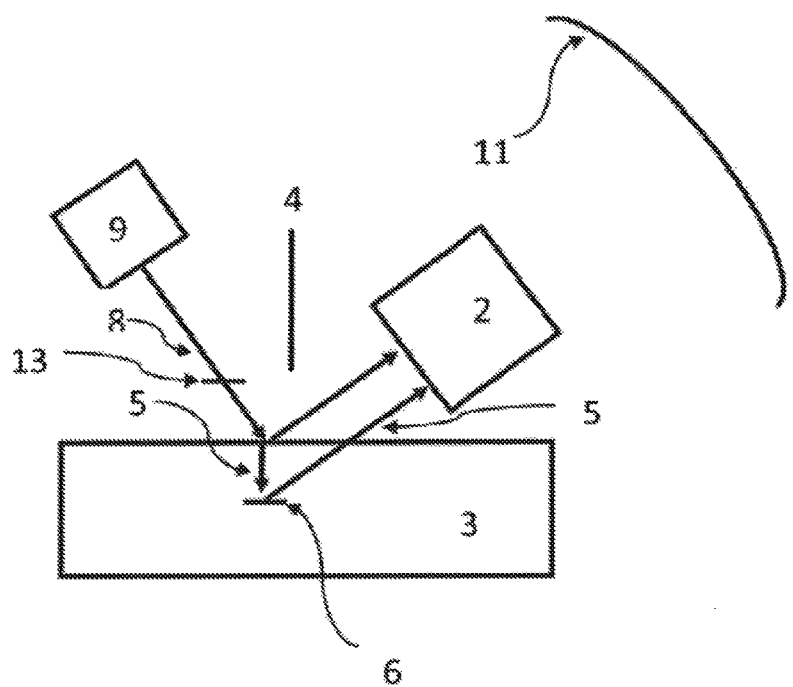
FIG. 5 shows another different apparatus.

FIG. 5 shows a different variant apparatus, where the generator is not a thermo-acoustic generator but a high-intensity laser, operated in short-pulse mode 9. The emitted laser beam 8 leads to a thermo-acoustic shock wave as soon as it makes contact with the medium of the test object 3. If the laser beam is focused in air and has sufficient energy, the beam itself (without additional medium other than air) can generate a plasma spark which leads to a shock wave. This shock wave is an acoustic wave 5 which is then detected by the means as described above. If, for a specific reason, the ultrasonic wave would not be generated by the direct contact of the laser beam 8 with the test object 3 (e.g. when the material of the test object is transparent to the laser beam), an absorption target 13 (which is not transparent) may be introduced into the laser beam 8. This absorption target 13 has the desired degree of absorption (usually a high degree of absorption) and will not be damaged by the laser beam 8. It generates a thermo-acoustic ultrasound acoustic wave 5, which has similar properties as an acoustic wave radiated from a generator (5, FIG. 4). The absorption target 13 or absorption plate may also be placed in the medium 10, or may even be buried inside the test object 3.

Further reference numerals in FIG. 5:
2: Membrane-free and resonance-free optical microphone (ultrasound receiver)
3: test object, material sample
4: Optional shielding wall
5: Ultrasound pressure wave
6: Material defect
8: Laser beam, generating a thermo-acoustic shock (5) wave at the surface of the test object (3)
9: Laser
11: Mirror element
13: Absorption target Possible variations of FIG. 5: the angles 14 (see FIG. 1) between emitter 1b and test object 3, or receiver 2 and test object 3, or emitter and receiver 3 may be varied in order to maximize a certain signal component.

the distance between laser 9, receiver 2 and test object 3 may be varied in order to maximize a certain signal component.

the laser 9 can preferably be guided coaxially along a receiver path for the receiver 2, wherein the angle between generator beam and receiving reflected sound waves is substantially 0°. With such embodiment, the laser beam from the generator 9 as well as a laser of the laser microphone are transmitted through one or two fibers to a single carrier 7 which holds the laser 9 and the sensor 2. Preferably, said carrier is mountable on a scanner device (FIG. 7) or could even be a handheld device.

the laser 9 may be operated in different pulse-length modes (ps, ns, and other) and at different optical wavelengths (e.g. at 1064 nm, 532 nm, the far-infrared, and other)

the laser 9 and the receiver 2 may be placed on opposing sides of the test object 3, resulting in a transmission-setup measurement.

the surface shape of the receiver 2 may be varied. It may be smaller or larger, according to the required detector sensitivity, or, it may take the shape of a sphere, of a plane, of a parabolic mirror or other.

additional mirror elements 11 may be placed in front of (or: behind of) the detector 2. These mirror elements can be planar or have a curved surface (for instance a parabolic shape). The mirrors may contain holes for excitation sound transmission, if required.

FIG. 6 shows a configuration of the membrane-free and resonance-free and resonance-free optical microphone. Sound pressure 5 is influencing the through-hole 15 optical properties, affecting the laser beam 16 of the optical microphone.

For details of the configuration of the membrane-free and resonance-free optical microphone, also refer to published patent applications WO2008000007A1, WO2010029509A1, WO2012163681A1.

Numeral 2 indicates a membrane-free and resonance-free optical microphone (ultrasound receiver); 5 indicates ultrasound pressure waves and 11 a mirror element.

15 indicates a through-hole in the microphone, filled with arbitrary medium (preferably gaseous media like air or fluid media like a liquid, as need may be even other media might be used) and 16 indicates a laser beam for interrogation of membrane-free and resonance-free optical microphone. The laser beam is either created directly by a laser diode on the microphone 2 or might be preferably delivered through an optical fiber.

Figure 7:
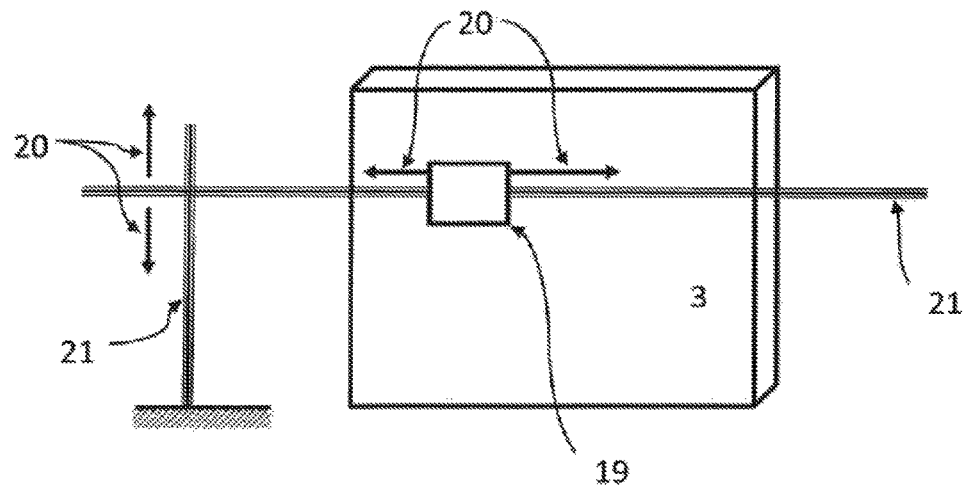
FIG. 7 shows a scanning system.

FIG. 7 shows a new scanner system employing the inventive combination of a sound generator made from a resonance-free thermo-acoustic ultrasound generator which does not rely on mechanically deformable or oscillating parts and a sound receiver made from a membrane-free and resonance-free optical microphone without any resonance effects in an air or gas coupled pulse echo arrangement. By the help of guide rails 21 or similar arrangements, the testing system 19 (refer to any of the devices of FIGS. 1, 2, 3 and 5) containing generator and receiver is moved over the surface of the test object 3 (material sample) along the directions of movement 20.

Figure 8:
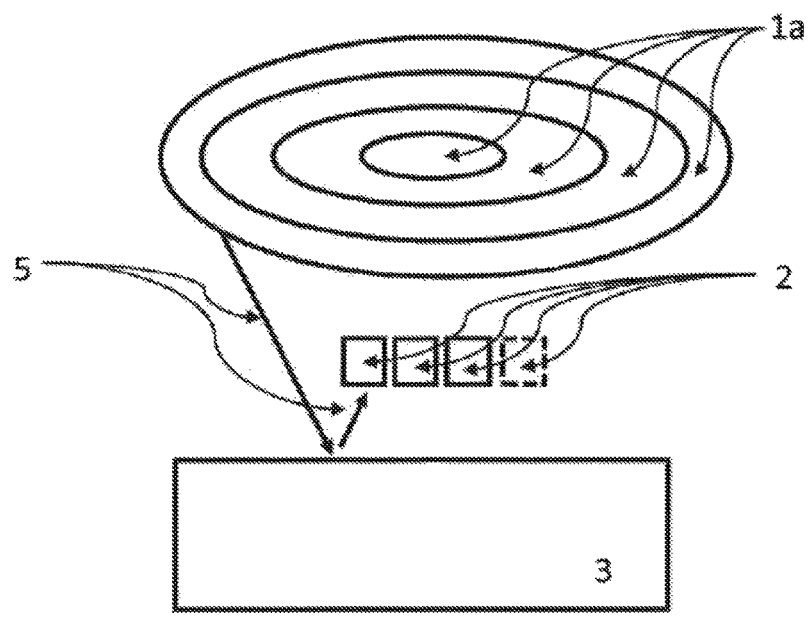
FIG. 8 shows an array system employing arrays of thermo-acoustic transducers and arrays of membrane-free and resonance-free optical microphones.

FIG. 8 illustrates an exemplary array system. In this configuration, the generator consists of two, three or more emitting elements 1a. These emitting elements 1a can be arranged side-by-side, or in a concentric manner as shown in FIG. 8. This so-called phased-array configuration allows to direct the emitted beam 5 into a specific desired spatial direction by controlling the phase between the single elements. It also allows to focus the beam 5 of the ultrasound pressure wave onto the surface of the test object 3. The detector 2 also consists of two, three, or more membrane-free and resonance-free optical microphones (ultrasound receivers). This detector configuration allows to analyze the differential signal, or to further improve the signal-to-noise ratio. It may also be used for beam-forming analysis or other techniques commonly used and known to experts in the field.

Further devices/variants and methods are described and covered in the claims.

What is claimed is:

1. An airborne ultrasound testing system for testing a test object, comprising:
   a sound generator for generating ultrasound waves in a test object;
   a sound receiver;
   a control arrangement to control both the sound generator and the sound receiver; and
   a computer assisted test result interface connected to the sound receiver to display an image of the test object derived from signals of the sound receiver;
   wherein the sound generator is a resonance-free ultrasound generator;
   wherein the sound receiver comprises a membrane-free optical microphone, said optical microphone comprising a source of electromagnetic radiation, a detector for detecting said electromagnetic radiation, and two spatially fixed mirrors, said two spatially fixed mirrors being spaced at a predefined distance from one another, said electromagnetic radiation being coupled into a space between said two spatially fixed mirrors, said electromagnetic radiation being influenced by an alteration of a refractive index of a gaseous or fluid medium, said alteration being induced by ultrasound waves emitted from the test object,
   wherein said sound generator and said sound receiver are arranged in an air or gas coupled pulse echo arrangement or in an air or gas coupled transmission mode arrangement.

2. The testing system of claim 1, wherein the sound generator is a pulsed laser beam which is guided coaxially along a receiver path for the sound receiver, wherein an angle between the pulsed laser beam and ultrasound waves emitted from the test object is substantially 0°, wherein the electromagnetic radiation of the optical microphone is a laser and the pulsed laser beam from the sound generator as well as a laser of the optical microphone are transmitted through one or two fibers to a single carrier which holds the sound generator and the optical microphone, wherein said carrier is mountable on a scanner device or wherein said carrier is a handheld device.

3. The testing system of claim 2, wherein more than one carrier with more than one sound generator and/or with more than one optical microphone are provided in array form.

4. The testing system of claim 1, wherein the sound receiver is mountable on a scanner.

5. The testing system of claim 1, wherein the sound receiver is a handheld device, said handheld device allowing for scanning.

6. The testing system of claim 1, further comprising a sound-shielding wall provided to isolate unwanted direct ultrasound waves of the sound generator from the emitted ultrasound waves of the test object.

7. The testing system of claim 1, wherein the sound generator and/or the sound receiver are arranged at an angle relative to a surface of the test object said angle can be varied with respect to the relative position of the sound generator and/or the sound receiver to said vertical plane on the test object.

8. The testing system of claim 7, wherein the sound generator and the sound receiver are arranged on a mechanical mount which provides means for adjusting the angle and/or the distance between the sound generator and the sound receiver and the test object, respectively.

9. The testing system of claim 1, wherein the sound generator is built as a concave curved generator, wherein the sound generator has a parabolic emitting element.

10. The testing system of claim 9, wherein the sound generator contains a foil in an order of µm-thickness and is formed into the shape of a curved, especially a parabolic emitter.

11. The testing system of claim 9, wherein the sound generator is mounted in front of a concave emitter-mirror, which reflects the ultrasound waves onto the test object.

12. The testing system of claim 1, wherein the sound receiver is subsequently arranged to the sound generator on a mechanical mount in direction to the test object, the sound receiver contains a hollow chamber or a through hole through which emitted ultrasound sound waves may propagate towards the test object.

13. The testing system of claim 1, wherein at least one reflection mirror is provided to direct and/or focus the emitted ultrasound sound waves onto the test object or from the test object onto the sound receiver or its space respectively.

14. The testing system of claim 13, wherein the mirror contains holes for ultrasound wave transmission.

15. The testing system of claim 1, wherein the sound receiver is mounted in front of the sound generator via a mechanical mount, so that the direction of the emitted ultrasound waves and the direction of the received ultrasound waves is at least substantially parallel.

16. The testing system of claim 1, wherein the sound generator contains two, three or more ultrasound emitting elements which are arranged side-by-side, or in a concentric manner as a phased-array configuration in order to allow to direct the emitted ultrasound waves into a specific desired spatial direction by controlling the phase between each of the ultrasound emitting elements, wherein the phased array configuration is controllable to allow to focus the emitted ultrasound waves onto the surface of the test object.

17. The testing system of claim 1, wherein the sound receiver comprises two, three, or more optical microphones, detecting the ultrasound waves induced alteration of the refractive index of the gaseous or fluid medium, the testing system comprises a control which allows to analyze a respective differential signal of the optical microphones, or to improve the signal-to-noise ratio.

18. The testing system of claim 1, further comprising a computer to display an image of the test object derived from signals of the sound receiver.

19. The testing system of claim 1, wherein the sound generator is a thermo-acoustic sound generator.

20. A method for testing a test object with ultrasound air pressure waves, comprising the steps of:
   providing a sound generator;
   providing a membrane-free and resonance free optical microphone as a sound receiver, said optical microphone comprising a source of electromagnetic radiation, a detector for detecting said electromagnetic radiation, and two spatially fixed mirrors, said two spatially fixed mirrors being spaced at a predefined distance from one another;

generating an ultrasound wave via the sound generator in the test object;

wherein the ultrasound wave is emitted from the test object, said emitted ultrasound wave generating ultrasound pressure waves;

detecting said generated ultrasound pressure waves via the optical microphone;

wherein said ultrasound pressure waves are detected via the optical microphone through an interaction of an electromagnetic radiation coupled into a space between said two spatially fixed mirrors, wherein said space contains a gaseous or fluid medium having a refractive index, wherein said refractive index is altered through an influence of the ultrasound pressure waves;

analyzing the detected ultrasound pressure waves; and displaying the analyzed ultrasound pressure waves.

21. The method of claim 20, wherein the sound generator emits a short or several short high-intensity laser pulse(s) onto the surface of the test object or any absorption target/plate introduced between said surface of the test object and the sound generator, or introduced inside the test object, in order to create there a thermo-acoustic shock wave as emitting ultrasound air pressure waves.

* * * * *